United States Patent
Jackson et al.

(10) Patent No.: US 11,972,563 B2
(45) Date of Patent: Apr. 30, 2024

(54) CONTRAST IMAGING SYSTEM AND METHOD

(71) Applicant: General Electric Company, Schenectady, NY (US)

(72) Inventors: John Irvin Jackson, Brookfield, WI (US); Amy Deubig, Waukesha, WI (US); John Londt, Oconomowoc, WI (US); Christine Carol Hammond, Waukesha, WI (US); Scott McOlash, Wauwatosa, WI (US); Vignesha Ramegowda, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 17/722,808

(22) Filed: Apr. 18, 2022

(65) Prior Publication Data

US 2022/0237794 A1 Jul. 28, 2022

Related U.S. Application Data

(62) Division of application No. 15/993,166, filed on May 30, 2018, now abandoned.

(51) Int. Cl.
*G06T 7/00* (2017.01)
*A61B 6/00* (2006.01)
(Continued)

(52) U.S. Cl.
CPC ............ *G06T 7/0012* (2013.01); *A61B 6/032* (2013.01); *A61B 6/06* (2013.01); *A61B 6/4035* (2013.01);
(Continued)

(58) Field of Classification Search
CPC ......... G06T 7/0012; G06T 2207/10081; A61B 6/032; A61B 6/06; A61B 6/4035;
(Continued)

(56) References Cited

U.S. PATENT DOCUMENTS 6,230,041 B1    5/2001   Prince
6,745,066 B1    6/2004   Lin
(Continued)

FOREIGN PATENT DOCUMENTS

CA          2577652 C    11/2015
CN       104866727 A    8/2015
(Continued)

OTHER PUBLICATIONS

CN patent application 201910419102.X filed May 20, 2019—Office Action dated Nov. 9, 2022, 9 pages.
(Continued)

*Primary Examiner* — Baisakhi Roy
*Assistant Examiner* — Kaitlyn E Sebastian

(57) ABSTRACT

An imaging system and method acquires non-contrast images of a region of interest in a body and determines an entrance criterion based on the non-contrast images. The entrance criterion dictates conditions in which to begin acquiring contrast imaging exposures of the region of interest. An amount of a contrast agent is measured in one or more locations in the imaged body subsequent to acquiring the non-contrast images. The system and method determine that the one or more conditions of the entrance criterion are met based on the amount of the contrast agent that is measured in the imaged body, and acquire one or more contrast images of the region of interest in the imaged body responsive to determining that the one or more conditions of the entrance criterion are met.

4 Claims, 6 Drawing Sheets

(51) Int. Cl.
*A61B 6/03* (2006.01)
*A61B 6/06* (2006.01)
*A61B 6/40* (2024.01)

(52) U.S. Cl.
CPC .............. *A61B 6/481* (2013.01); *A61B 6/541* (2013.01); *G06T 2207/10081* (2013.01)

(58) Field of Classification Search
CPC ......... A61B 6/481; A61B 6/541; A61B 6/486; A61B 6/5288; A61B 6/542; A61B 6/545; A61B 6/504; A61B 6/482; A61B 6/503; A61B 6/5217; A61B 6/469; A61B 6/037; A61B 6/44; A61B 6/4417; A61B 6/501; A61B 6/507; A61B 6/508; A61B 6/5235; A61B 6/54; G16H 50/30
See application file for complete search history.

(56) References Cited

U.S. PATENT DOCUMENTS

| | | | |
|---|---|---|---|
| 6,904,306 | B1 | 6/2005 | Wu |
| 6,968,225 | B2 | 11/2005 | Vu |
| 7,095,892 | B2 | 8/2006 | Lee |
| 7,110,806 | B2 | 9/2006 | Prince |
| 7,457,657 | B2 | 11/2008 | Harder |
| 7,529,394 | B2 | 5/2009 | Krishnan |
| 7,949,167 | B2 | 5/2011 | Krishnan |
| 8,655,071 | B2 | 2/2014 | Ferman |
| 9,589,374 | B1 | 3/2017 | Gao |
| 9,668,699 | B2 | 6/2017 | Georgescu |
| 9,848,843 | B2 | 12/2017 | Grass |
| 2006/0064018 | A1* | 3/2006 | Chomas ................. A61B 8/481 600/459 |
| 2006/0274878 | A1* | 12/2006 | Hsieh ..................... A61B 6/541 378/8 |
| 2007/0242153 | A1 | 10/2007 | Tang |
| 2008/0119715 | A1 | 5/2008 | Gonzalez Molezzi |
| 2009/0124898 | A1 | 5/2009 | Stodilka |
| 2009/0253983 | A1 | 10/2009 | Foo |
| 2010/0290686 | A1 | 11/2010 | Canstein |
| 2011/0058647 | A1* | 3/2011 | Star-Lack .............. G16H 50/30 378/65 |
| 2012/0219222 | A1 | 8/2012 | Ferman |
| 2015/0201895 | A1 | 7/2015 | Suzuki |
| 2017/0000440 | A1 | 1/2017 | Okerlund |
| 2017/0086772 | A1* | 3/2017 | Vaz ...................... A61B 6/5217 |
| 2017/0086775 | A1 | 3/2017 | Madhav |
| 2017/0209113 | A1* | 7/2017 | Jackson ................. A61B 5/024 |

FOREIGN PATENT DOCUMENTS

| | | |
|---|---|---|
| CN | 103619257 B | 6/2016 |
| EP | 2189112 A1 | 5/2010 |
| WO | 9917809 W | 4/1999 |
| WO | 201706645 W | 1/2017 |

OTHER PUBLICATIONS

Ko, B. et al., "Combined CT Coronary Angiography and Stress Myocardial Perfusion Imaging for Hemodynamically Significant Stenoses in Patients With Suspected Coronary Artery Disease—A Comparison With Fractional Flow Reserve," JACC: Cardiovascular Imaging, vol. 5, No. 11, Nov. 2012, 15 pages.

* cited by examiner

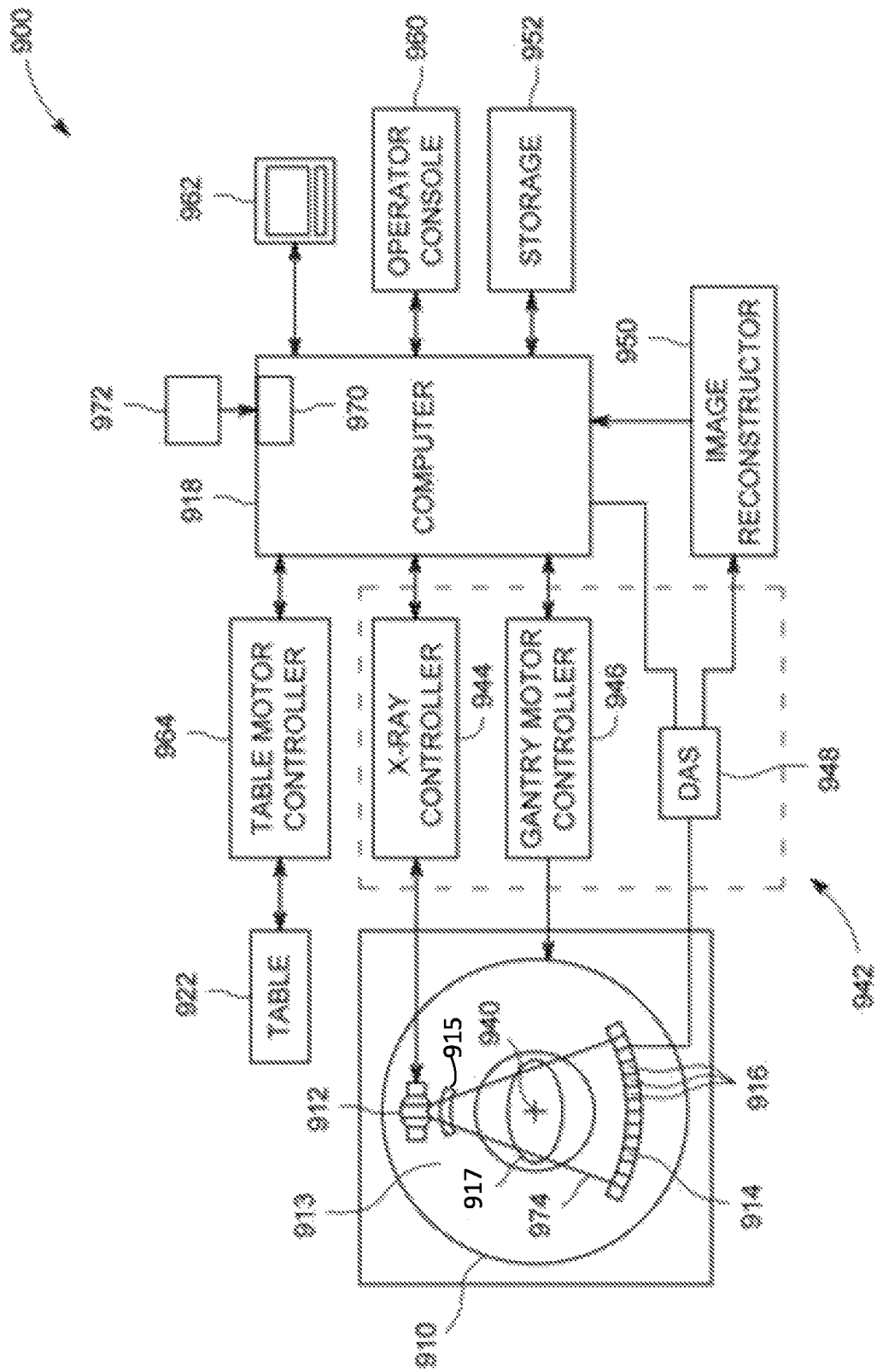

CONTRAST IMAGING SYSTEM AND METHOD

CROSS-REFERENCE TO RELATED APPLICATIONS

The present application is a divisional application of and claims priority to U.S. patent application Ser. No. 15/993,166, filed on May 30, 2018, the entirety of which is incorporated herein by reference.

FIELD

The subject matter disclosed herein relates generally to imaging systems, and more particularly to imaging systems that use or rely on introduction of contrast agents into imaged bodies to obtain image data.

BACKGROUND

Contrast agents can be introduced into imaged bodies to improve contrast density in image data generated by imaging systems. Because the introduction of a contrast agent into an imaged body is not instantaneous, the imaging of a body with a contrast agent can be reliant on timing to ensure that a sufficient amount of the contrast agent has reached a region of interest in the body before imaging begins.

Scanning too early or too late may not achieve the desired imaging enhancement provided by the contrast agent. In some types of imaging, such as computed tomography (CT) perfusion scanning, timing the image scans with the flow of the contrast agent through the body can be problematic when looking to scan at different phases of blood flow (arterial versus venous phases, for example). Currently, operators of the imaging systems apply general rules determined through trial and error as to when to begin each group of image scans in an imaging following administration of the contrast agent.

In patients having atypical blood flow rates, following these general rules may result in failure to image at the correct time, and a re-scan may be required. For example, in perfusion scanning, several phases of scanning are performed. Each phase collects a set or group of imaging scans at the same location with a specific time interval between the scans for some length of time having a minimum and/or maximum duration. As another example, cardiac scans can have an additional constraint of needing the imaging to occur at a certain heart cycle, which can impact the duration of the imaging scan.

The general rules used today to determine when to begin the first of several imaging scans focus or rely on the initial arrival of the contrast agent at a monitored location. But, this does little to nothing to assist the imaging system operator to determine the appropriate start time for subsequent groups of imaging scans or for ending a group of imaging scans. Imaging during the incorrect time can result in a re-scan of the region of interest.

When a rescan is needed, however, the operator may need to wait for the already administered contrast agent to clear from the imaged body before attempting to re-scan the body. Additionally, this can result in a patient receiving multiple doses of the contrast agent and radiation. At high volume imaging sites, this can result in significant delay and interference with the imaging workflows of the sites.

BRIEF DESCRIPTION

In one embodiment, a method includes acquiring one or more non-contrast images of a region of interest in an imaged body and determining an entrance criterion based on the one or more non-contrast images. The entrance criterion dictates one or more conditions in which to begin acquiring one or more groups of contrast imaging exposures of the region of interest in the imaged body. The method also includes measuring an amount of a contrast agent in one or more locations in the imaged body subsequent to acquiring the one or more non-contrast images of the region of interest in the imaged body, determining that the one or more conditions of the entrance criterion are met based on the amount of the contrast agent that is measured in the imaged body, and acquiring one or more contrast images of the region of interest in the imaged body responsive to determining that the one or more conditions of the entrance criterion are met.

In one embodiment, an imaging system includes one or more processors configured to examine one or more non-contrast images of a region of interest in an imaged body and to determine an entrance criterion based on the one or more non-contrast images. The entrance criterion dictates one or more conditions in which to begin acquiring one or more groups of contrast imaging exposures of the region of interest in the imaged body. The one or more processors also are configured to measure an amount of a contrast agent in one or more locations in the imaged body after acquiring the one or more non-contrast images of the region of interest in the imaged body and to determine that the one or more conditions of the entrance criterion are met based on the amount of the contrast agent that is measured in the imaged body. The one or more processors also are configured to direct an imaging source and an imaging detector to acquire one or more contrast images of the region of interest in the imaged body responsive to determining that the one or more conditions of the entrance criterion are met.

In one embodiment, a method includes acquiring image data of a region of interest in an imaged body by exposing the region of interest to multiple imaging exposures within one or more groups of imaging exposures with the imaging exposures in each of the groups separated in time by one or more temporal delays, changing the one or more temporal delays in at least one of the groups of the imaging exposures based on one or more of a heart rate of a patient having the imaged body, an average or median of the one or more temporal delays, or a measured amount of a contrast agent in the imaged body, and forming one or more images of the region of interest using the image data.

BRIEF DESCRIPTION OF THE DRAWINGS

The inventive subject matter described herein will be better understood from reading the following description of non-limiting embodiments, with reference to the attached drawings, wherein below:

FIG. 6 is a block schematic diagram of one example of a CT imaging system that may be utilized to implement various embodiments discussed herein.

DETAILED DESCRIPTION

Figure 1:
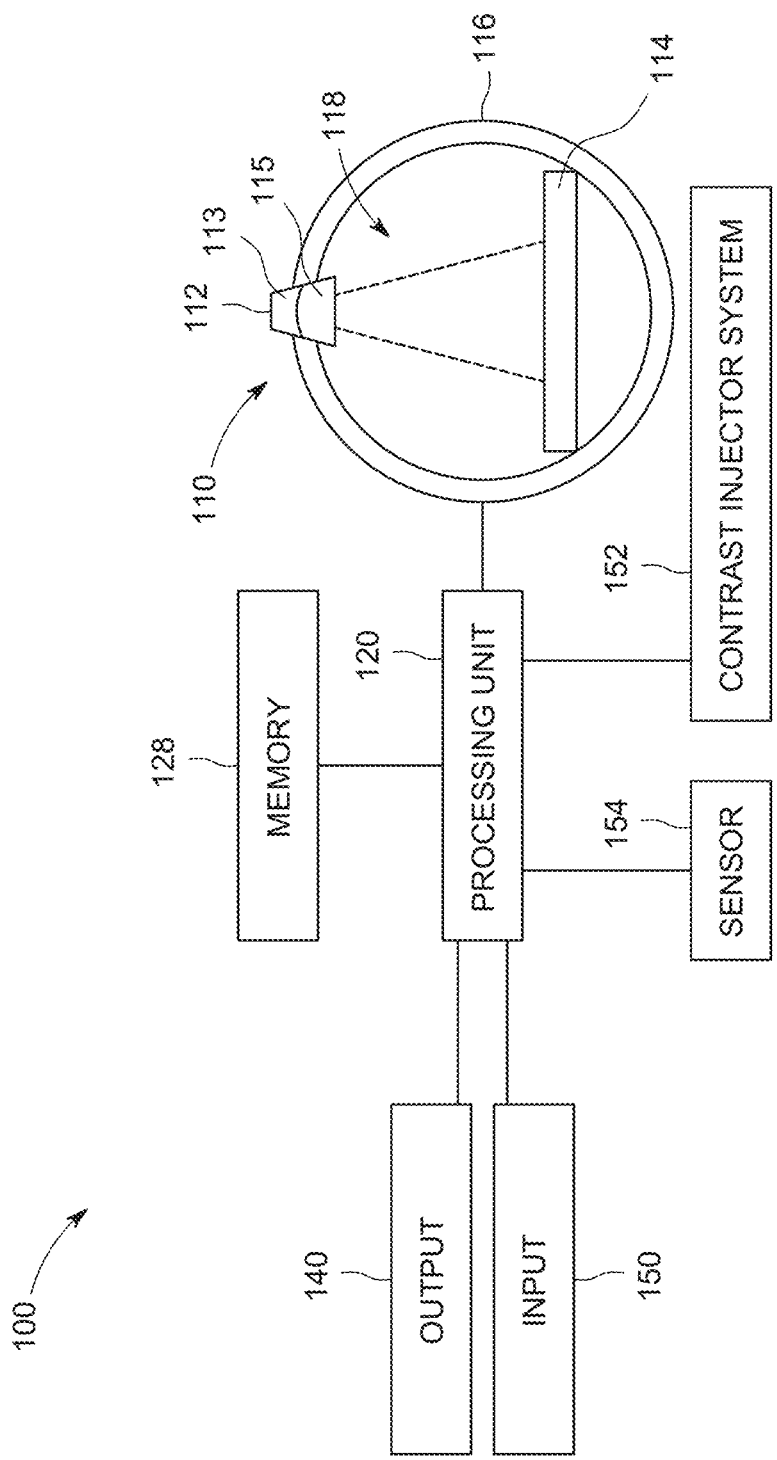
FIG. 1 illustrates an imaging system in accordance with one embodiment of the inventive subject matter described herein.

One or more embodiments of the inventive subject matter described herein provide for contrast imaging systems and methods that determine entrance and/or exit criteria for one or more groups of imaging scans in an imaging series. The series can include a single group of imaging scans, or multiple groups of imaging scans that are to be obtained at different times. Each group of the imaging scans can include one or more exposures of an imaged body to an imaging energy source, such as x-ray radiation.

The entrance criteria can define when the imaging system is to begin the first group of imaging scans and/or when to begin any of one or more of the groups of imaging scans. The exit criteria can define when the imaging system is to end one group of imaging scans and optionally when to begin the next group of imaging scans. The exit criteria optionally can be referred to as transitional criteria. While the description herein focuses on perfusion scanning and cardiac imaging, optionally, one or more embodiments of the inventive subject matter may be used for other types of contrast imaging (e.g., images acquired using the administration of a contrast agent into an imaged body).

In one embodiment, the entrance and/or exit criteria can be determined prior to the start of diagnostic scanning using one or more non-contrast images of a region of interest or another scan location. Contrast images include images acquired after administration (e.g., injection) of one or more contrast agents into the imaged body (e.g., the patient) to enhance image contrast, while non-contrast images include images that are acquired without any contrast agent being administered (e.g., no contrast agent is injected within several minutes or hours prior to the scanning). The system or an operator of the system can select a location or region of interest on the non-contrast images and specify criteria in terms of the contrast level (e.g., the Hounsfeld unit, or HU level of radioactivity from the contrast agent) that is computed at the region of interest, in terms of the elapsed time, and/or in terms of the number of scans to be acquired. More than one location or region of interest may be specified.

With respect to the entrance criteria, the contrast agent can be administered to a patient and the imaging system can subsequently acquire one or more monitor scans of the region or location of interest prior to starting to acquire imaging scans of the group associated with the entrance criteria. The system can calculate the amount of contrast agent (e.g., the HU level) in the specified region(s) or location(s) of interest as the monitor scans are acquired. When the entrance criteria are met based on the measured amount of contrast agent, the system will automatically trigger the start of scanning of the group associated with the entrance criteria.

With respect to the exit criteria, the system will calculate the amount of contrast agent in the specified region(s) or location(s) of interest in the imaging scans being acquired for the current group. When the exit criteria are met based on the measured amount of contrast agent in the specified location(s), the system will stop scanning for the current group (even if the number of scans that were prescribed for that group has not yet completed) and automatically trigger the start of scanning of the next group. The system can permit the operator to manually override the automatic trigger to start the transition to the next group if the operator determines that the transition to the next group should occur sooner.

The systems and methods can provide real-time monitoring and condition criteria logic to ensure that transitions between imaging groups occur when the contrast enhancement reaches a needed level for the groups. The criteria logic can be augmented by patient modeling and prior patient information to reduce the number of monitor scans that are needed. For example, characteristics of the patient being imaged, such as age, gender, heart rate, disease state, etc., can be determined and compared to a model formed from many previous imaging sessions with the same and/or other patients. The timings for when to begin and when to transition between different groups of imaging scans can be associated with different regions of interest being imaged, with different sets of patient characteristics, and the like. These timings can be used to define or determine the entrance and/or exit criteria for a patient by comparing the characteristics of the patient to the model. This can allow for fewer monitor scans to be obtained of the patient while determining when to begin or transition between imaging groups, thereby reducing the exposure of the patient to imaging radiation. Additionally, this can provide for more consistent imaging results across a variety of different patients. This also can reduce the errors in imaging when there is an incorrect contrast level in a region of interest, thereby reducing the number of needed re-scans of the patient.

FIG. 1 illustrates an imaging system 100 in accordance with one embodiment of the inventive subject matter described herein. The imaging system 100 may be configured, for example, to perform computed tomography (CT) scanning of an object, such as a human or animal patient (or portion thereof), such as CT scanning for a perfusion study or cardiac study. The imaging system 100 includes a CT acquisition unit 110 and a processing unit 120. The CT acquisition unit 110 acquires projection data or imaging data (e.g., CT data or CT imaging information), while the processing unit 120 controls operation of the CT acquisition unit 110, and reconstructs images using the data acquired by the CT acquisition unit 110. Various embodiments may include additional components, or may not include all the components shown in FIG. 1 (for example, various embodiments may provide sub-systems for use with other sub-systems to provide an imaging system). Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The CT acquisition unit 110 includes an X-ray source 112 and a CT detector 114. The X-ray source 112 and the CT detector 114 (along with associated components such as bowtie filters, source collimators, detector collimators, or the like) may rotate about a central axis of a bore of a gantry 116 of the system 100. The depicted X-ray source 112 includes a generator 113 and a tube 115. The generator 113 may be used to control (e.g., via input signals from the processing unit 120) the supply of power to the tube 115 to change the energy level or voltage level of the tube 115. For example, the X-ray source 112 may be utilized to provide varying energy levels during rotation of the CT acquisition unit 110 around an object to be imaged. In some embodiments, the X-ray source 112 may be configured to be switched between a high voltage (e.g., a nominal 140 kV) and a low voltage (e.g., a nominal 80 kV) as the CT acquisition unit 110 is rotated about an object to be imaged and used to collect a series of projections of the object. In some embodiments, the voltage may be switched from view to view as the CT acquisition rotates (e.g., a given view at the high voltage or energy level, the immediately subsequent view at the low voltage or energy level, the next immediately subsequent view at the high voltage or energy level, and so forth).

X-rays from the X-ray source 112 may be guided to an object to be imaged through a source collimator and bowtie filter. The object to be imaged, for example, may be a human patient, or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 112 to control distribution of X-rays passed to the object to be imaged.

X-rays that pass through the object to be imaged are attenuated by the object and received by the CT detector 114 (which may have a detector collimator associated therewith), which detects the attenuated X-rays and provides imaging information to the processing unit 120. The processing unit 120 may then reconstruct an image of the scanned portion of the object using the imaging information (or projection information) provided by the CT detector 114. The processing unit 120 may include or be operably coupled to the output device 140, which in the illustrated embodiment is configured to display an image, for example, an image reconstructed by the processing unit 120 using imaging information from the CT detector 114. The input device 150 is configured to obtain input corresponding to a scan to be performed, with the processing unit 120 using the input to determine one or more scan settings (e.g., tube voltage, tube current, scanning rotation speed, or the like). The input device 150 may include a keyboard, mouse, touchscreen or the like to receive input from an operator, and/or may include a port or other connectivity device to receive input from a computer or other source.

In the illustrated embodiment, the X-ray source 112 is configured to rotate about the object. For example, the X-ray source 112 and the CT detector 114 may be positioned about a bore 118 of the gantry 116 and rotated about the object to be imaged. As the X-ray source 112 rotates about the object during an imaging scan, X-rays received by the CT detector 114 during one complete rotation provide a three hundred sixty-degree view of X-rays that have passed through the object. Other imaging scanning ranges may be used in alternative embodiments. The CT imaging information may be collected as a series of views that together make up a rotation or portion thereof. Each view or projection may have a view duration during which information (e.g., counts) is collected for the particular view. The view duration for a particular view defines a CT information acquisition period for that particular view. For example, each rotation may be made up of about one thousand views or projections, with each view or projection having a duration or length of about one thousandth of a complete rotation.

The processing unit 120 represents hardware circuitry that includes and/or is connected with one or more processors (e.g., one or more integrated circuits, one or more microprocessors, and/or one or more field programmable gate arrays) that control various aspects of the CT acquisition unit 110 and/or to reconstruct an image using information obtained via the CT acquisition unit 110. For example, the processing unit 120 may be configured to reconstruct a CT image using information collected by the CT acquisition unit 110. The processing unit 120 is operably coupled to the input device 150, the output device 140, and the CT acquisition unit 110. The processing unit 120, for example, may receive information regarding a scan from the input device 150 that may be utilized in determining a desired clinical task, patient information, and/or scanning parameters to be used for a given imaging scan to be performed with the imaging system 100. As another example, the processing unit 120 may receive imaging data or projection data from the CT detector 114. As one more example, the processing unit 120 may provide control signals to one or more aspects of the CT acquisition unit 110, such as the X-ray source 112 and CT detector 114. The processing unit 120 may include processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may be distributed among various units or housings.

The processing unit 120 controls the CT acquisition unit 110 (e.g., by controlling the activation and deactivation of the X-ray source 112, as well as the energy or voltage level of the X-ray source 112), and collects CT imaging information during an imaging scan. In various embodiments, the processing unit 120 may control the CT acquisition unit 110 to first obtain a scout projection or scan of an object to be imaged to help determine one or more characteristics of the object (e.g., size, attenuation levels, or the like).

The processing unit 120 optionally controls operation of a contrast injector system 152. The contrast injector system 152 includes one or more devices that can be controlled to automatically administer one or more contrast agents into an imaged body, such as a vein of a patient. For example, the contrast injector system 152 can include one or more reservoirs or containers of a contrast agent fluidly coupled with a plunger that forces the contrast agent from the reservoir into the imaged body. The imaged body may have one or more ports, catheters, intravenous conduits, or the like, through which the contrast agent can be administered to the imaged body. The processing unit 120 can generate and send control signals to the injector system 152 to direct the injector system 152 to automatically inject the contrast agent into the imaged body. Alternatively, the processing unit 120 can generate signals that direct the output device 140 to visually and/or audibly present instructions to an operator who can manually administer the contrast agent to the imaged body based on the instructions. One or more sensors 154 can be operatively coupled with the processing unit 120 by one or more wired and/or wireless connections. These sensors 154 can measure characteristics of the imaged body, such as a heart rate of a patient. For example, the sensors 154 can represent leads of an electrocardiograph.

Figure 2:
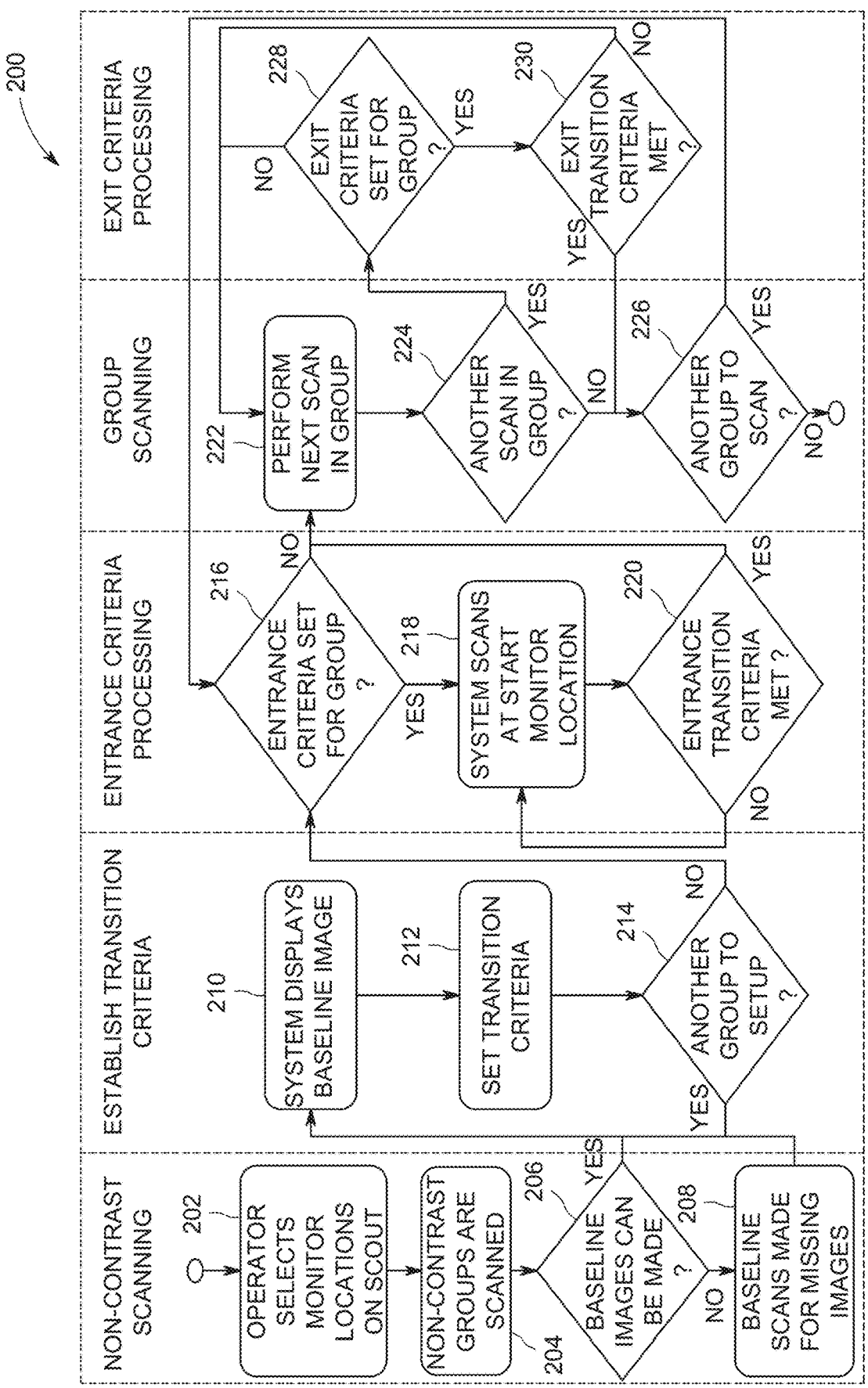
FIG. 2 illustrates a flowchart of one embodiment of a method for performing contrast imaging of an imaged body.

FIG. 2 illustrates a flowchart of one embodiment of a method 200 for performing contrast imaging of an imaged body. The method 200 can be used to direct the operations of the imaging system 100, such as the operations performed and/or controlled by the processing unit 120, in determining when to begin one or more image scans in a group of scans and/or when to transition between groups of image scans based on measured contrast levels in the imaged body.

At 202, one or more monitor locations are selected on a scout image. The scout image can be an image of in the imaged body that is obtained prior to a contrast agent being administered into the imaged body or before an administered contrast agent reaches an imaged volume in the imaged body. The imaged volume can be the area or volume of the body that is to be imaged using the contrast agent. The non-contrast scout image can be obtained, and an operator of the system 100 (shown in FIG. 1) or the processing unit 120 (shown in FIG. 1) can identify one or more locations in the scout image as the monitor locations. In one embodiment, the monitor locations are places in the imaged body where the amount of contrast agent (e.g., the contrast level) is measured to determine whether the entrance or exit criteria have been met for the imaged body.

Figure 3:
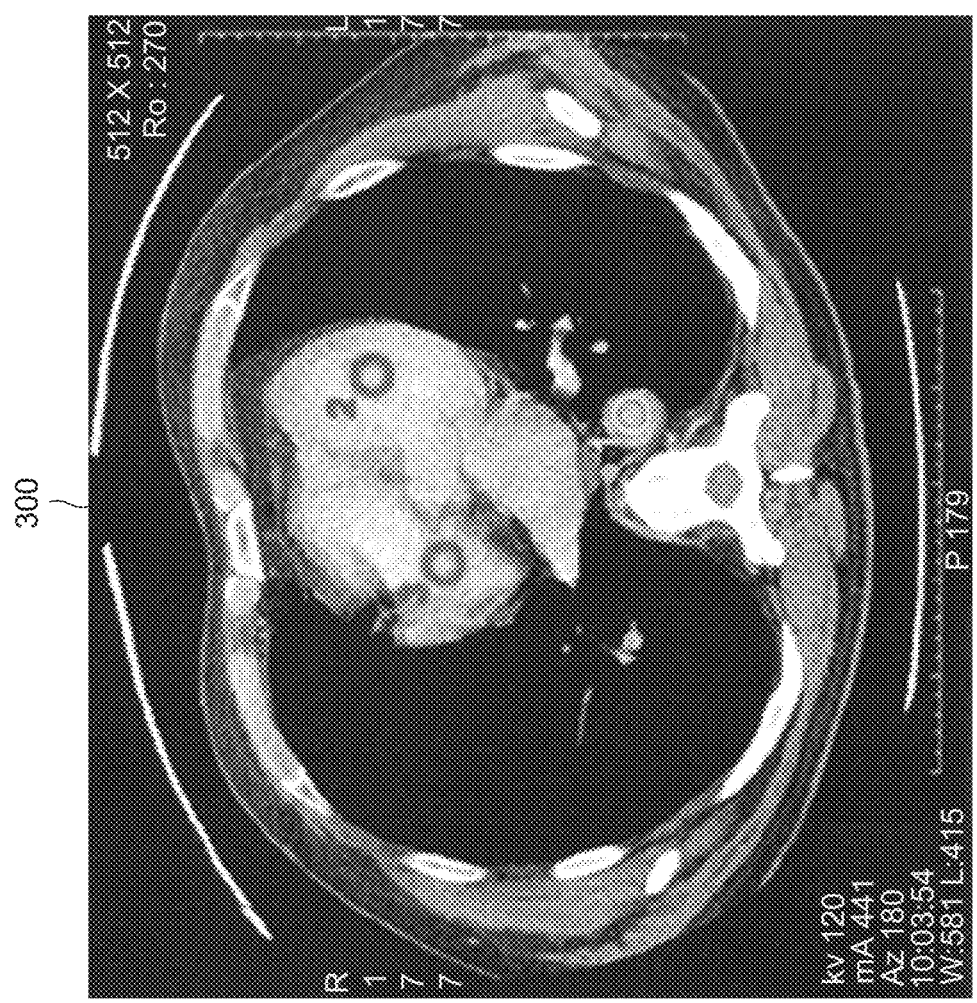
FIG. 3 illustrates one example of a non-contrast image obtained of the imaged body.

With continued reference to the flowchart of the method 200 shown in FIG. 2, FIG. 3 illustrates one example of a non-contrast image 300 obtained of the imaged body. The non-contrast image 300 can be the scout image referred to at 202 in the method 200. The non-contrast image 300 can be a scan from a perfusion study of a human patient in one embodiment. Alternatively, the non-contrast image 300 can be a scan of another anatomy of the patient or of another imaged body. As described above, the non-contrast image 300 is obtained prior to injecting or otherwise administering a contrast agent into the region of interest that is shown in the image 300, or after injecting the contrast agent but before the contrast agent reaches the region of interest shown in the image 300.

Several monitor locations labeled 1, 2, and 3 are shown on the non-contrast image 300 shown in FIG. 3. These monitor locations can be manually selected by an operator of the imaging system 100, or may be automatically selected by the processing unit 120 of the imaging system 100. For example, the output device 140 may display the image 300 and the operator of the imaging system may use the input device 150 to select locations in the image 300 for the monitor locations. As another example, the input device 150 and the output device 140 may be a single device, such as a touchscreen, and the operator of the imaging system may touch the locations on the image 300 where the monitor locations are to be located.

Optionally, the processing unit 120 of the imaging system 100 may automatically select the monitor locations from the non-contrast image 300. The processing unit 120 may examine characteristics of pixels, voxels, or other units of the image 300 to determine where the monitor locations are to be located. For example, the processing unit 120 may determine intensity levels, colors, or the like, of the pixels in the image 300, and compare these characteristics with each other and/or to one or more thresholds. The monitor locations may be selected based on these comparisons, such as by locating a monitor location in an area where the pixel characteristics exceed or fall below a threshold, or are different from neighboring pixels by at least a designated amount.

Returning to the description of the flowchart of the method 200 shown in FIG. 2, at 204, one or more non-contrast groups of imaging scans are obtained. For example, the processing unit 120 can direct the acquisition unit 110 to obtain one or more non-contrast images of the imaged body by exposing the body to one or more doses of radiation. These doses optionally can be referred to herein as pulses of imaging radiation. These non-contrast groups of imaging scans can be obtained prior to administration of a contrast agent into the imaged body, or after administration of the contrast agent into the imaged body but before the contrast agent has reached the portion of the body being imaged.

At 206, a determination is made as to whether one or more baseline images can be created from the non-contrast groups of imaging scans. The baseline images can be used for comparison purposes to determine how the amount of contrast, or the contrast level, has changed at the monitor locations. The determination of whether the non-contrast group of imaging scans can be used to create the baseline image or images can be based on one or more characteristics of the non-contrast scans. For example, this determination can be based on whether the region of interest is shown in the non-contrast scans, whether one or more, or all, of the monitor locations are shown in the non-contrast scans, or the like.

If one or more baseline images can be created from the non-contrast groups of image scans, then no additional non-contrast images may need to be acquired of the imaged body in one embodiment. As a result, flow of the method 200 can proceed from 206 toward 210. But, if one or more baseline images cannot be created from the non-contrast group of image scans, then one or more additional non-contrast image scans may need to be acquired. As a result, flow the method 200 can proceed from 206 toward 208.

At 208, one or more baseline scans created for the missing images. The missing images may be the non-contrast groups of imaging scans obtained at 204 that are not used or not useful for the baseline scans. For example, the processing unit 120 can direct the acquisition unit 110 to acquire one or more additional non-contrast images of the imaged body as the one or more baseline scans.

At 210, at least one of the baseline images is presented. For example, the processing unit 120 can direct the output device 140 to visually display at least one of the baseline images. This display of a baseline image can be performed so that the operator of the imaging system 100 can verify that the monitor locations are acceptable to the operator and/or are visible in the baseline image. If the displayed baseline image is not acceptable, then flow of the method 200 can return toward one or more of the operations 202, 204, 206, or 208. For example, the operator can provide input into the input device 150 indicating that the displayed baseline image is unacceptable. Optionally, the method 200 does not include the display operation described in connection with 210. Instead, flow of the method can proceed from 206 or 208 toward 212.

At 212, one or more imaging criteria are determined. The imaging criteria determined at 212 can include the exit criteria described herein. The exit criteria define one or more rules that, if met or otherwise satisfied, cause imaging system 100 (a) to automatically stop exposing the imaged body to pulses or scans of imaging radiation to complete the acquisition of the one or more images in the group of an imaging series, (b) to automatically transition to the next group of images and an imaging series, or (c) to both stop exposing imaged body to imaging radiation to complete a currently acquired group and an imaging series and to automatically begin exposing the imaged body to imaging radiation to begin acquisition of images in the next group in the imaging series.

The exit criteria can include a variety of different rules. As one example, the exit criteria for a group of imaging exposures or scans can include contrast level rules that are satisfied if the contrast level at a monitor location or a combination of monitor locations in the imaged body exceeds one or more thresholds, falls below one or more thresholds, changes by more or less than a designated rate, includes a peak, or the like.

The exit criteria can be defined by the operator of the imaging system 100, can be default rules for the imaging system 100, can be default rules for the type of imaged body, can be default rules based on one or more characteristics of the patient having the imaged body, or the like. For example, the operator of the imaging system 100 can use the input device 150 to provide the rules that define the exit criteria for a single or multiple groups of imaging scans. As another example, each imaging system 100 or several imaging systems 100 can have the same exit criteria defined as default or fallback rules, which optionally may be modified by the operator of imaging system 100, may be modified by the processing unit 120 based on one or more patient models, or a combination thereof. With respect to the characteristics of the patient having imaged body, the processing unit 120 may obtain characteristics of the patient, such as the patient's age, gender, type of body part being imaged, heart rate, or other physiological measurements or indicators. The processing unit 120 optionally can store this information in the memory 128, and/or can obtain one or more criteria models stored in the memory 128.

The criteria models can be relationships between patient characteristics, details of different imaging series, and the exit criteria. For example, a criteria model may be established by examining previous imaging series on one or more different patients. The previous imaging series can be examined by determining the characteristics of the patients being imaged in the different imaging series. These different imaging series also can be examined to determine the anatomy being imaged as the imaged body of the different patients. The imaging series also may be examined to determine how long it took for the contrast agents in the different patients to reach the different imaged bodies after administering the contrast agent, and optionally how long it took for the contrast agents to reach certain designated levels in the different imaged bodies of the different patients.

This model can provide a corpus of information that can assist the processing unit 120 of the imaging system 100 to determine how much contrast agent is to be measured at one or more monitor locations in the imaged body before transitioning to the next or other group of image scans in the imaging series (e.g., the exit criteria). For example, the processing unit 120 can compare the age, gender, heart rate, or the like, of a patient is about to be imaged, with the same or similar characteristics of many different patients whose data forms part of the model. The processing unit 120 also can compare the imaged body of the patient that is about to be imaged with the different imaged bodies of the many different patients whose data forms the model.

The processing unit 120 can then select or identify (from the model) the contrast levels (used to begin or transition to a group of imaging scans) at one or more monitor locations in the patients having the same or similar characteristics and/or the same or similar imaged body parts as the patient is about to be imaged. The processing unit 120 can then use these model-derived contrast levels to determine the contrast level threshold(s) used to determine when to transition between groups of imaging scans for the patient to be imaged (e.g., the exit criteria).

Optionally, the model can indicate how long it will take for a contrast agent to reach a designated level in one or more monitor locations of an imaged body that is to be imaged based on a comparison of the characteristics of the patients, the types of imaged bodies, and the like. For example, processing unit 120 can compare the age, gender, heart rate, or the like, of a patient is about to be imaged, with the same or similar characteristics of many different patients whose data forms part of the model. The processing unit 120 also can compare the imaged body of the patient is about to be imaged with the different imaged bodies of the many different patients whose data forms the model. The processing unit 120 can then select or identify from the model how long it took for the contrast agent to reach the certain designated levels at the monitor locations in the patients having the same or similar characteristics and/or the same or similar imaged body parts as the patient is about to be imaged. The processing unit 120 can then use the time delay between administering the contrast agent and when the contrast agent reached certain designated levels in the patients forming the model to determine when to switch between different groups of imaging exposures in the series for the patient to be imaged.

In another example, the exit criteria can include one or more limits or restrictions on the number of scans to complete in one or more imaging groups. One exit criterion can be a lower limit on the number of imaging scans to capture during a group. This exit criterion may require that at least this lower limit of imaging scans be obtained by the imaging system 100 (e.g., by the detector 114) before the imaging system 100 is permitted to proceed to the next imaging group (or terminate the imaging series). This lower limit can be defined by the operator, can have a default value based on the type of body being imaged, or can be defined in another way. Until this lower limit is reached by the number of imaging scans obtained in an imaging group, the processing unit 120 may prevent the imaging system 100 from proceeding to the next group in the imaging series. Optionally, the processing unit 120 may otherwise prevent the imaging system 100 from completing the imaging series.

Another exit criterion can include an upper limit on the number of imaging scans to capture during the group. This exit criterion can prevent more than this upper limit of imaging scans from being obtained by the imaging system 100 during an imaging group. This upper limit can be defined by the operator, can have a default value based on the type of body being imaged, or can be defined in another way. Once this exit criterion is met, the processing unit 120 may automatically direct imaging system 100 to proceed to the next imaging group or terminate the imaging series.

An exit criterion can be a lower temporal limit on how long acquiring the imaging scans in a group can last. For example, this exit criterion can prevent the processing unit 120 from directing the imaging system 100 to complete a currently imaged group and proceed to a subsequent image group before this lower temporal limit is reached. This can prevent the imaging system 100 from terminating an imaging group too early, and optionally may prevent the imaging system 100 from beginning a subsequent imaging group before the contrast level in the imaged body reaches one or more thresholds.

An exit criterion can be an upper temporal limit on how long acquiring the imaging scans in a group can last. For example, this exit criterion can prevent the processing unit 120 from continuing to direct the imaging system 100 to acquire additional scans in a currently, unfinished imaging group if the time elapsed since beginning the imaging group exceeds the upper temporal limit. This can prevent the imaging system 100 from dwelling too long in obtaining scans for an imaging group. Dwelling too long in an imaging group can run the risk of the contrast level in one or more monitor locations falling too low for a subsequent imaging group. If this were to occur, there may not be enough contrast agent in a monitor location for a subsequent imaging group to provide increased image contrast in the scans of the subsequent imaging group. In one embodiment, if the time elapsed since beginning the imaging for a current group has reached the upper temporal limit, the processing unit 120 can direct imaging system 100 to automatically terminate the current group and proceed to begin acquiring imaging scans for the next, subsequent group in the image series.

Returning to the description of the flow chart of a method 200 shown in FIG. 2, the exit criteria can be determined (at 212) individually for each group of imaging scans or exposures in a series of several groups of imaging scans or exposures. For example, each group of imaging scans may have a separate and potentially different exit criterion or criteria defined for that group. The exit criteria for each group can be different from the exit criteria for all other groups, or two or more (or all) imaging groups can have the same exit criteria. While several exit criteria can be determined for an imaging group, optionally, a single exit criterion can be determined for an imaging group.

At 214, a determination is made as to if there is another group of imaging scans or exposures for which the exit criteria are yet to be determined. For example, the previous determination of the criteria at 212 may be for a first, second, third, or so on, group of imaging exposures in the series of several groups of imaging exposures. The determination at 214 involves deciding whether there is another, next, or subsequent group of imaging exposures in the series.

If there is an additional group of imaging exposures for which the exit criteria need to be determined, then flow of the method 200 can proceed from 214 back toward 208. For example, one or more additional baseline images may be created from the non-contrast group of images obtained at 204 for the additional, subsequent, or next group of imaging exposures. At 210, the baseline image or images are displayed, and at 212, exit criteria for this currently examined group of upcoming imaging exposures are determined. In this way, flow the method 200 can proceed in a loop involving 208, 210, 212, 214 that determines the exit criteria for each of one or more groups o imaging exposures in the series of several groups of imaging exposures. In one embodiment, at 214, once the exit criteria have been determined for all groups of the imaging exposures to occur for the patient or imaged body to be imaged, then flow of the method 200 can proceed from 214 toward 216.

At 216, a determination is made as to whether the entrance criteria have been set for the group of imaging exposures. The entrance criteria define one or more rules that, if met or otherwise satisfied, cause the imaging system 100 automatically begin exposing the imaged body to imaging radiation to acquire one or more images in a group of imaging series. In contrast to the exit criteria which define when performance of a series of imaging exposures is to proceed from one group of imaging exposures to the next group of imaging exposures, the entrance criteria can define when the first group of imaging exposures is to begin.

In one embodiment, the entrance criterion or criteria may be determined only for the first group of imaging scans to be obtained in an imaging series. This entrance criterion or criteria can define or otherwise dictate when the very first imaging group is to be obtained in the imaging series, but not when any other imaging group is to be obtained. As described herein, the exit or transition criteria can define when to end an imaging group (and proceed to the next imaging group in a series), when to transition between imaging groups in the series, or when to otherwise begin another imaging group in the series. Alternatively, one or more entrance criteria can be determine for one or more imaging groups other than or in addition to the first imaging group in a series.

The entrance criteria can include a variety of different rules. As one example, the entrance criteria for the first group of imaging exposures or scans in a series can include contrast level rules that are satisfied when the measured contrast level at one or more of the monitor locations in the imaged body exceeds one or more thresholds, falls below one or more thresholds, increases by a rate faster than a designated rate, decreases by a rate slower than a designated rate, includes a peak (e.g., an increase followed by a decrease), or the like.

The entrance criteria can be defined by the operator of the imaging system 100, can be default rules for the imaging system 100, can be default rules for the type of imaged body, can be default rules based on one or more characteristics of the patient having the imaged body, or the like. For example, the operator the imaging system 100 can use the input device 150 to provide the rules that define the entrance criteria for a first group of imaging scans. As another example, each imaging system 100 or several imaging systems 100 can have the same entrance criteria defined as default or fallback rules, which optionally may be modified by the operator of imaging system 100, may be modified by the processing unit 120 based on one or more patient models, or a combination thereof.

As described above with respect to the exit criteria, the criteria models can be mathematical relationships between patient characteristics, details of different imaging series, and the entrance criteria for previous imaging series on the same or other patients. The processing unit 120 can compare the age, gender, heart rate, or the like, of a patient is about to be imaged, with the same or similar characteristics of many different patients whose data forms part of the model. The processing unit 120 also can compare the imaged body of the patient is about to be imaged with the different imaged bodies of the many different patients whose data forms the model. The processing unit 120 can then select or identify (from the model) the contrast levels (used to begin or transition to a group of imaging scans) at one or more monitor locations in the patients having the same or similar characteristics and/or the same or similar imaged body parts as the patient is about to be imaged. The processing unit 120 can then use these model-derived contrast levels to determine the contrast level threshold(s) used to determine when to begin the first group of imaging scans for the patient to be imaged (e.g., the entrance criteria).

Optionally, the model can indicate how long it will take for a contrast agent to reach a designated level in one or more monitor locations of an imaged body that is to be imaged based on a comparison of the characteristics of the patients, the types of imaged bodies, and the like. The processing unit 120 can compare the age, gender, heart rate, or the like, of a patient is about to be imaged, with the same or similar characteristics of many different patients whose data forms part of the model. The processing unit 120 also can compare the imaged body of the patient is about to be imaged with the different imaged bodies of the many different patients whose data forms the model. The processing unit 120 can then select or identify from the model how long it took for the contrast agent to reach the certain designated levels at the monitor locations in the patients having the same or similar characteristics and/or the same or similar imaged body parts as the patient is about to be imaged. The processing unit 120 can then use the time delay between administering the contrast agent and when the contrast agent reached certain designated levels in the patients forming the model to determine when to begin acquiring the first group of imaging exposures for the patient to be imaged.

Another entrance criterion can include an upper limit on the number of scans to be obtained for an imaging group. If the number of scans for an imaging group that is input into the imaging system 100 (for example, via the input device 150) exceeds this upper limit, then the processing unit 120 can prevent acquisition of imaging scans in the first imaging group from beginning. The processing unit 120 optionally can prompt the operator of the imaging system 100 to correct, update, modify, or otherwise change the number of scans to be obtained for the first imaging group.

If it is determined (at 216) that the entrance criteria have not been determined, set, or otherwise established, then flow of the method 200 can proceed toward 222. Optionally, the entrance criteria can be determined, set, or otherwise established at 216 if the entrance criteria have not already been set. If it is determined (at 216) that the entrance criteria have been determined, set, or otherwise established, then flow of the method 200 can proceed toward 218. While the description herein states that several entrance criteria may be determined, alternatively, a single entrance criterion can be determined for the first imaging group.

At 218, a monitor image is acquired of a region of interest in the imaged body. The monitor image can be an image that is acquired using the imaging system 100 under the direction of the processing unit 120. The imaged body can be exposed to imaging radiation to generate the image data representative of the monitor image after the contrast agent has been administered into the imaged body. The monitor image can be acquired to investigate whether the contrast agent has reached one or more monitor locations in the imaged body, to investigate the amount of the contrast agent at the one or more monitor locations, and/or to otherwise determine changes in the contrast level at the one or more monitor locations.

At 220, a determination is made as to whether the entrance criteria for the first group of imaging exposures in the series has been met or reached. As one example, the determination can involve examining whether the contrast level in one or more of the monitor locations (for example, monitor locations 1, 2, 3 shown in FIG. 1) has reached or exceeded a corresponding, designated contrast level threshold, whether the contrast level is increasing faster (or, alternatively, slower) than a designated rate, whether the changes in the contrast level with respect to time include a peak, or the like.

In one example, the processing unit 120 can measure the amount of contrast agent that appears in a monitor image at one or more of the monitor locations 1, 2, 3 previously identified at 202. Optionally, the processing unit 120 can measure the amount of contrast agent that appears in the monitor image at one or more other locations. The processing unit 120 can automatically determine the amount of contrast agent appearing in a location in the monitor image based on characteristics of pixels or voxels in the monitor image, such as the intensity, color, or the like, of the pixels or voxels.

The processing unit 120 optionally may translate, rotate, or otherwise change an orientation or position of an image scan so that one or more locations (e.g., the center position) of the monitor image and/or subsequent scans are the same. This assists the processing unit 120 in registering the images so that the monitored location is in a consistent and persistent place in the monitor images and subsequent scans.

The processing unit 120 optionally can normalize the measured contrast levels in the monitor and/or subsequent images. Normalizing the contrast levels can prevent a contrast level in a monitor or other image from being incorrectly measured as larger or smaller than the contrast level actually is. The processing unit 120 may compute the contrast levels in a relatively short period of time, such as five hundred milliseconds or less. This can help ensure that the criteria can be compared with the measured contrast levels in a timely manner and before the contrast level in one or more monitor locations significantly changes.

The processing unit 120 can determine whether the measured amount of contrast level in one or more of the monitor locations 1, 2, 3 exceeds one or more corresponding, designated contrast level thresholds. Optionally, the processing unit 120 can determine whether the measured amount of contrast level in 2 or more of the monitor locations exceeds a combination of the corresponding, designated contrast level thresholds.

If the measured level of contrast in the one or more the monitor locations, or in a combination of the monitor locations, exceeds one or more corresponding thresholds, then the entrance criteria may have been met. This can indicate that there is now sufficient contrast agent in the imaged body to begin exposing the imaged body to imaging radiation for the first group of imaging exposures. As a result, flow of the method 200 can proceed from 220 toward 222. But, if the measured level of contrast in the one or more monitor locations (or in a combination of the monitor locations) does not exceed one or more corresponding thresholds, then the entrance criteria may not have been met. This can indicate that there is not yet sufficient contrast agent in the imaged body to begin exposing the imaged body imaging radiation for the first group of imaging exposures. As a result, flow of the method 200 can proceed from 220 back to 218. For example, the method 200 can proceed in a loop between 218 and 220 to repeatedly acquire additional monitor images of the imaged body, repeatedly measure the contrast level at one or more monitor locations in the monitor images, and repeatedly determine whether the measured contrast level has reached or exceeded one or more designated thresholds, until or unless the entrance criteria has been met.

Figure 4:
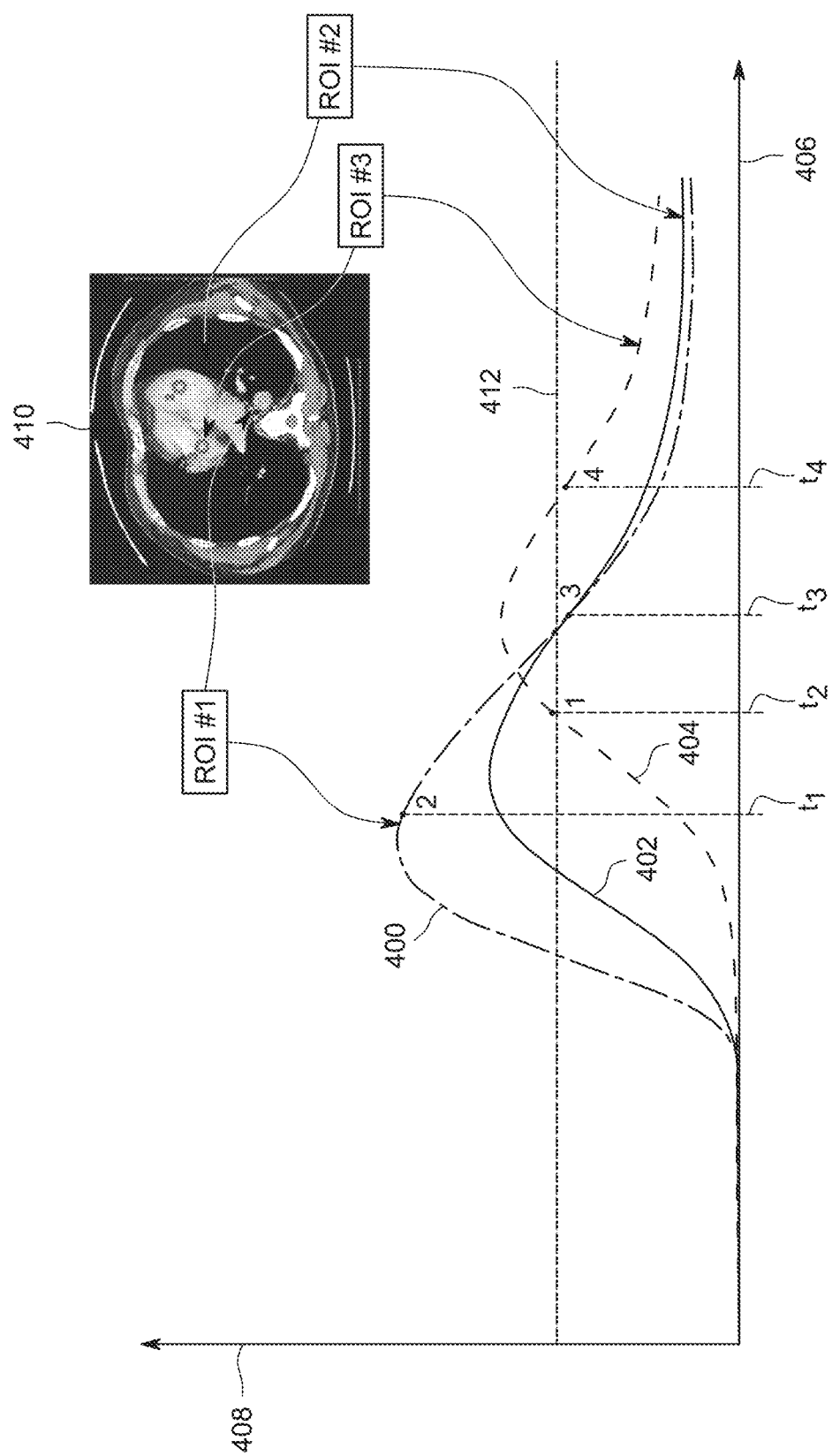
FIG. 4 illustrates one example of several contrast levels measured at the different monitoring locations in monitor images at different times.

FIG. 4 illustrates one example of several contrast levels 400, 402, 404 measured at the different monitoring locations 1, 2, 3 in the monitor images at different times. Each of the contrast levels 400, 402, 404 represents the amount of contrast agent measured at a different monitoring location 1, 2, 3 in one or more monitor images 410. The monitor image 410 can be an image of an imaged body that was acquired at 218. In the illustrated embodiment, the contrast levels 400, 402, 404 are shown alongside a horizontal axis 406 indicative of time or sample number (e.g., the number of monitor images 410 acquired) and are shown alongside a vertical axis 408 indicative of increasing contrast levels.

The contrast levels 400 can represent the amount of contrast agent that is measured at different times at the first monitor location 1 in the monitor images 410. The contrast levels 402 can represent the amount of contrast agent that is measured at different times at the second monitor location 2 in the monitor images 410. The contrast levels 404 can represent the amount of contrast agent that is measured at different times at the third monitor location 3 in the monitor images 410. In FIG. 4, the first monitor location 1 is labeled as ROI #1, indicating that the first monitor location 1 is a first region of interest in the imaged body. The second monitor location 2 is labeled as ROI #2, indicating that the second monitor location 2 is a second region of interest in the imaged body. The third monitor location 3 is labeled as ROI #3, indicating that the third monitor location 3 is a third region of interest in the imaged body. Optionally, a single monitor location can be examined, two monitor locations can be examined, or more than three monitor locations can be examined.

In one embodiment, the output device 140 can display the monitor images 410 with the monitor locations 1, 2, 3 labeled and shown on the image 410 on the output device 140. This can assist the operator of imaging system 100 to visually monitor changes in the contrast levels at these monitor locations 1, 2, 3, and optionally to determine whether any abnormalities in delivery of the contrast agent have occurred. Several monitor images obtained at different times can be presented in a sequence (e.g., a video or other time-based combination of image frames) to show the operator how the contrast level at one or more of the monitor locations changes with respect to time.

A contrast level threshold 412 also as shown in FIG. 4. As described above, the processing unit 120 compare the measured contrast levels 400, 402, and/or 404 in one or more different monitor images 410 at different times to determine when one or more of the measured contrast levels 400, 402, and/or 404 exceed the threshold 412. As one example, the entrance criteria can include a single rule or criterion, such as a requirement that the contrast level 400 measured at the first monitor location 1 exceeds the designated threshold 412. The contrast level 400 first exceeds the threshold 412 at a time $t_1$ in FIG. 4. In this example, the processing unit 120 may determine that the entrance criteria are met at the time $t_1$ and may then trigger the beginning of the first group of imaging exposures in the series. With respect to the flowchart of the method 200 shown in FIG. 2, this can result in the method 200 proceeding from 220 toward 222.

As another example, the entrance criteria can require that the contrast levels 400, 402, 404 measured at each of the monitor locations 1, 2, 3 concurrently exceed the threshold 412. Stated differently, this entrance criteria can require that the contrast levels 400, 402, 404 are all above the threshold 412 at the same time. This first occurs in FIG. 4 at a time $t_2$. The processing unit 120 may determine that the entrance criteria is met at the time $t_2$ and may then trigger the beginning of the first group of imaging exposures in the series. With respect to the flowchart of the method 200 shown in FIG. 2, this can result in the method 200 proceeding from 220 toward 222.

In another example, the entrance criteria can require that one or more contrast levels fall below the threshold 412 (after being above the threshold 412) and that one or more other contrast levels are above the threshold 412. For example, the entrance criteria can require that the contrast level 404 at the third monitor location 3 be above the threshold 412 but the contrast level 402 at the second monitor location 2 concurrently be above the contrast threshold 412 (or optionally, the first contrast level 402 at the first monitor location 1 to be below threshold 412). This first occurs in FIG. 4 at a time $t_3$. The processing unit 120 may determine that the entrance criteria is met at the time $t_3$ and may then trigger the beginning of the first group of imaging exposures in the series. With respect to the flowchart of the method 200 shown in FIG. 2, this can result in the method 200 proceeding from 220 toward 222.

In another example, the entrance criteria can require that one or more contrast levels falls below the threshold 412 (after being above the threshold 412). For example, the entrance criteria can require that the contrast level 404 at the third monitor location 3 be below the threshold 412 after being above the threshold 412. This first occurs in FIG. 4 at a time $t_4$. The processing unit 120 may determine that the entrance criteria is met at the time $t_4$ and may then trigger the beginning of the first group of imaging exposures in the series. With respect to the flowchart of the method 200 shown in FIG. 2, this can result in the method 200 proceeding from 220 toward 222.

The preceding examples are merely a few different entrance criteria that may be used to determine when to automatically begin the first group of imaging scans. Optionally, one or more other entrance criteria can be used. For example, an entrance criterion can be a rate of change in the measured contrast level at a monitor location. A designated positive rate of change can represent a rate at which the contrast level is expected to rise at a monitor location (e.g., based on the model described above or as otherwise set). If the contrast level is increasing at a rate that is faster than the positive designated rate, then the processing unit 120 can determine that the contrast level at the monitor location will exceed a designated contrast level threshold sooner than expected. As a result, the processing unit 120 can trigger the commencement of the first group of imaging scans (e.g., before the measured contrast level at that monitor location exceeds the contrast level threshold). But, if the contrast level is increasing at a rate that is slower than the designated rate, then the processing unit 120 can determine that the contrast level at the monitor location will exceed a designated contrast level threshold later than expected. As a result, the processing unit 120 can delay triggering commencement of the first group of imaging scans.

As another example, an entrance criterion can be detection of a peak in one or more of the measured contrast levels. The peak in a measured contrast level can be detected by the processing unit 120 identifying a positive, increasing slope or rate of change in a measured contrast level followed by a decreasing slope or rate of change in the same measured contrast level. The peak can be identified by the processing unit 120 as the largest contrast level between these increasing and subsequently decreasing rates of change. Alternatively, the processing unit can identify the peak as the contrast level between the increasing and subsequently decreasing rates of change that is larger than some, but not all, other contrast levels measured at the same location at different times.

In another example, an entrance criterion can be a sign of a rate of change in one or more of the measured contrast levels. For example, the processing unit 120 can determine whether a measured contrast level is increasing or decreasing with respect to time, and determine that at least one entrance criterion is met or satisfied when the contrast level is increasing (i.e., positive sign) or decreasing (i.e., negative sign) with respect to time.

The processing unit 120 can modify one or more thresholds of the entrance and/or exit criteria described herein as functions of the energy at which the imaging radiation is generated by the tube 115 of the imaging system 100. For example, a first, lower threshold may be used in the entrance and/or exit criteria while the tube 115 generates x-rays at a first, lower power level; a second, larger threshold may be used in the entrance and/or exit criteria while the tube 115 generates x-rays at a second, greater power level; a third, larger threshold may be used in the entrance and/or exit criteria while the tube 115 generates x-rays at a third, even greater power level; and so on.

Returning to the description of the method 200 shown in FIG. 2, at 222, an imaging scan in the currently imaged group of imaging scans is acquired. The processing unit 120 can direct the acquisition unit 110 of the imaging system 100 to expose the imaged body to imaging radiation, such as x-rays, to acquire image data. This image data can represent an imaging scan in the group of imaging scans. The image data can be recorded (e.g., stored) in the memory 128 and optionally displayed on the output device 140.

At 224, a determination is made as to whether the group includes one or more additional imaging scans. The imaging series can include one or more groups of imaging scans, with each group including a single imaging exposure or multiple imaging exposures. If the group being currently imaged includes only a single scan or includes several scans with the last scan in the group being previously obtained at 222, then flow of the method 200 can proceed toward 226. If the group being currently imaged includes one or more additional scans, then flow of the method 200 can proceed toward 228.

At 226, a determination is made as to whether there is another group of imaging scans in the imaging series currently being imaged. If the recently completed group of imaging scans is the only group in the series or is the last group in the series (with the other groups in the series being completed), then flow of the method 200 can terminate or can return toward 202. If the recently completed group is not the only group in the series and is not the last group in the series, then flow of the method 200 can proceed toward 216.

Returning to the description of the decision made at 224, if there are one or more additional scans to be performed in the group currently being imaged, then a determination is made (at 228) as to whether the exit criteria has been set or otherwise established for the currently imaged group. If exit criteria for the current group being imaged has been established (for example, at 212), then flow of the method 200 can proceed toward 230. If the exit criteria for the current group being imaged has not been established, then flow of the method 200 can return toward 222. For example, the processing unit 120 can direct imaging system 100 to continue collecting imaging scans for the group being currently imaged until the upper limit on the number of scans for this group has been reached.

At 230, a determination is made as to whether the exit criteria have been met for the group being currently imaged. As one example, this determination can involve examining whether the contrast level in one or more of the monitor locations (for example, monitor locations 1, 2, 3 shown in FIG. 1) in one or more of the imaging scans of the current group has reached or exceeded a corresponding, designated contrast level threshold. In contrast to the determination at 220 (that involved examining contrast levels in the monitor images), the determination at 230 can involve measuring contrast levels at one or more locations (e.g., the monitor locations) in the scans of the currently imaged group.

For example, the processing unit 120 can measure the amount of contrast agent that appears in a scan of the current group at one or more of the monitor locations 1, 2, 3. Optionally, the processing unit 120 can measure the amount of contrast agent that appears in the scan of the current group at one or more other locations. The processing unit 120 can determine the amount of contrast agent appearing in a location in the scan of the current group based on characteristics of pixels or voxels in the monitor image, such as the intensity, color, or the like, of the pixels or voxels. The processing unit 120 can determine whether the measured amount of contrast level in one or more of the monitor locations 1, 2, 3 is at or below one or more corresponding, designated contrast level thresholds. Optionally, the processing unit 120 can determine whether the measured amount of contrast level in two or more of the monitor locations does not exceed a combination of the corresponding, designated contrast level thresholds.

If the measured level of contrast in the one or more the monitor locations, or in a combination of the monitor locations, does not exceed one or more corresponding thresholds, then the exit criteria may have been met. As a result, flow of the method 200 can proceed from 230 toward 226. But, if the measured level of contrast in the one or more monitor locations (or in a combination of the monitor locations) does exceed one or more corresponding thresholds, then the exit criteria may not have been met. As a result, flow of the method 200 can proceed from 230 toward 222. For example, the method 200 can return to obtain additional scans in the currently imaged group until the exit criteria for the group is met.

With respect to the examples of contrast levels 400, 402, 404 shown in FIG. 4, the exit criteria can require that the contrast level 400 at the first monitor location 1 no longer exceeds the threshold 412. This can result in the exit criteria being met at the time $t_3$. Optionally, the exit criteria can require that the contrast levels 400, 402 at the first and second monitor locations 1, 2 both no longer exceed the threshold 412. This also can result in the exit criteria being met at time $t_3$.

In another example, the exit criteria can require that one or more contrast levels falls below the threshold 412 after being above the threshold 412. For example, the exit criteria for a group can require that the contrast level 404 at the third monitor location 3 be below the threshold 412 after being above the threshold 412. This occurs in FIG. 4 at a time $t_4$. The processing unit 120 may determine that the exit criteria are met at the time $t_4$ and may then trigger the end of the current group of imaging exposures in the series.

As another example, an exit criterion can be a required rate of change in the measured contrast level at a monitor location. If the contrast level is decreasing at a rate that is faster than a designated rate, then the processing unit 120 can determine that the exit criterion for the current group is met. As a result, the processing unit 120 can trigger the end of the current group of imaging scans.

In another example, an exit criterion can require detection of a peak in one or more of the measured contrast levels. Detection of such a peak can cause the processing unit 120 to terminate the current imaging group. As another example, an exit criterion can be a required sign of a rate of change (positive or negative) in one or more of the measured contrast levels. For example, the processing unit 120 can determine whether a measured contrast level is increasing or decreasing with respect to time, and determine that at least one exit criterion is met or satisfied when the contrast level is increasing (i.e., positive sign) or decreasing (i.e., negative sign) with respect to time.

As described above, the exit criteria can require one or more limits on the temporal duration of an imaging group and/or a number of scans to obtain in the imaging group. The processing unit 120 can use these limits to determine whether to terminate or continue a group being currently imaged. For example, if the time elapsed since beginning to acquire image data for a currently imaged group has not yet reached a temporal limit for the group, then imaging of the current group may continue. Otherwise, imaging of the current group can end. As another example, if the number of scans for a currently imaged group has not yet reached an upper limit on the number of scans for the group, then imaging of the current group may continue. Otherwise, imaging of the current group can terminate.

If it is determined (at 230) that the exit criterion or criteria for the group being currently imaged have been met or satisfied, then imaging of the current group can terminate and flow of the method 200 can proceed toward 226. As described above, the method 200 can determine at 226 whether additional groups are to be imaged. If it is determined (at 230) that the exit criteria for the group being currently imaged have not been met or satisfied, then imaging of the current group can continue and flow of the method 200 can return toward 222. As described above, the method 200 can obtain additional scans in the current group at 222.

Optionally, the processing unit 120 can automatically direct one or more other non-imaging actions based on the comparison between the measured contrast levels and the entrance and/or exit criteria. For example, the processing unit 120 can automatically direct additional contrast agent to be administered to the patient (and/or can provide instructions to the operator of the imaging system 100 to administer additional contrast agent via the output device). If the measured contrast levels are not increasing at a rapid enough rate (e.g., increasing slower than a designated positive rate) or are decreasing too quickly (e.g., decreasing faster than another designated negative rate), then the processing unit 120 can direct that additional contrast agent be administered to the imaged body. This can occur by the processing unit 120 waiting a designated period of time to allow the existing contrast agent to exit from the body and then generating and communicating a control signal to the injector system 152. This control signal can direct the injector system 152 to automatically administer additional contrast agent into the imaged body or patient. Alternatively, this signal can be communicated to the output device 140 to visually present instructions to the operator of the imaging system 100 to administer additional contrast agent to the patient.

In addition to or as an alternate to using measured contrast levels to determine when to begin or end an imaging group (or when to transition to the next imaging group), one or more embodiments of the inventive subject matter described herein relate to controlling the inter-scan timings during an imaging group. The inter-scan timings represent the temporal delay between image scans or exposures to imaging radiation within the same imaging group. As described above, an imaging group can include several image scans. These image scans can be acquired by exposing the imaged body to imaging radiation at different times. The time delay between these exposures can be referred to as an inter-scan timing.

The inter-scan timing can be a time period between consecutive scans in an imaging group. If the inter-scan timing does not change within an imaging group, the timing can be referred to as a static or non-changing inter-scan timing. In another embodiment, the inter-scan timing can change based on one or more patient characteristics, such as the heart rate of the patient, the age of the patient, the gender of the patient, the disease state of the patient, or the like. With respect to the heart rate, the inter-scan timing can require that imaging exposures occur once every cardiac cycle of the patient, once every other cardiac cycle of the patient, one every third cardiac cycle of the patient, once every $N^{th}$ cardiac cycle of the patient, and so on. In one embodiment, the inter-scan timing can dynamically change during or within an imaging group. For example, if the heart rate of the patient changes during acquisition of an imaging group, then the inter-scan timing can change with the changing heart rate. The heart rate of the patient can be monitored by one or more sensors that are coupled with the processing unit 120.

As another example, the processing unit 120 can specify that a sequence of exposures in an imaging group occur at an inter-scan timing that is based on different categories of patient characteristics. For example, the processing unit 120 can direct the acquisition unit 110 to generate radiation exposures once every heart beat while the heart rate of the patient is between a first limit and a second limit, once every other heart beat while the heart rate of the patient is between the second limit and a third limit, once every third heart beat while the heart rate of the patient is between the third limit and a fourth limit, and so on.

The processing unit 120 optionally can vary the inter-scan timing within a group such that the inter-scan timing can change within the group, but the average, median, mode, or other statistical measure of the inter-scan timing is at a designated value or within a designated range of the designated value (e.g., within 1%, within 3%, or within 5%). For example, the processing unit 120 can set a target inter-scan timing delay between scans of a group. During acquisition of the scans in the group, the inter-scan timing may change due to changes in the patient's heart rate and/or the need to acquire scans of a desired phase of the cardiac cycle of the patient. If the inter-scan timing is static and unchanging during the group, then considerable timing error in the scan acquisition can occur and the desired phase of the cardiac cycle may not be correctly imaged. The processing unit 120 can change the inter-scan timing during the group so that the average, median, or mode of the inter-scan timings in the group is equal to or within the range of the designated inter-scan timing. For example, if the inter-scan timing from one scan to the next scan in the group is slightly shorter or longer than the designated inter-scan timing, the inter-scan timing between the next scans in the same group can be lengthened or shortened so that the average, median, or mode of the inter-scan timing is equal to or within the range of the designated inter-scan timing.

Figure 5:
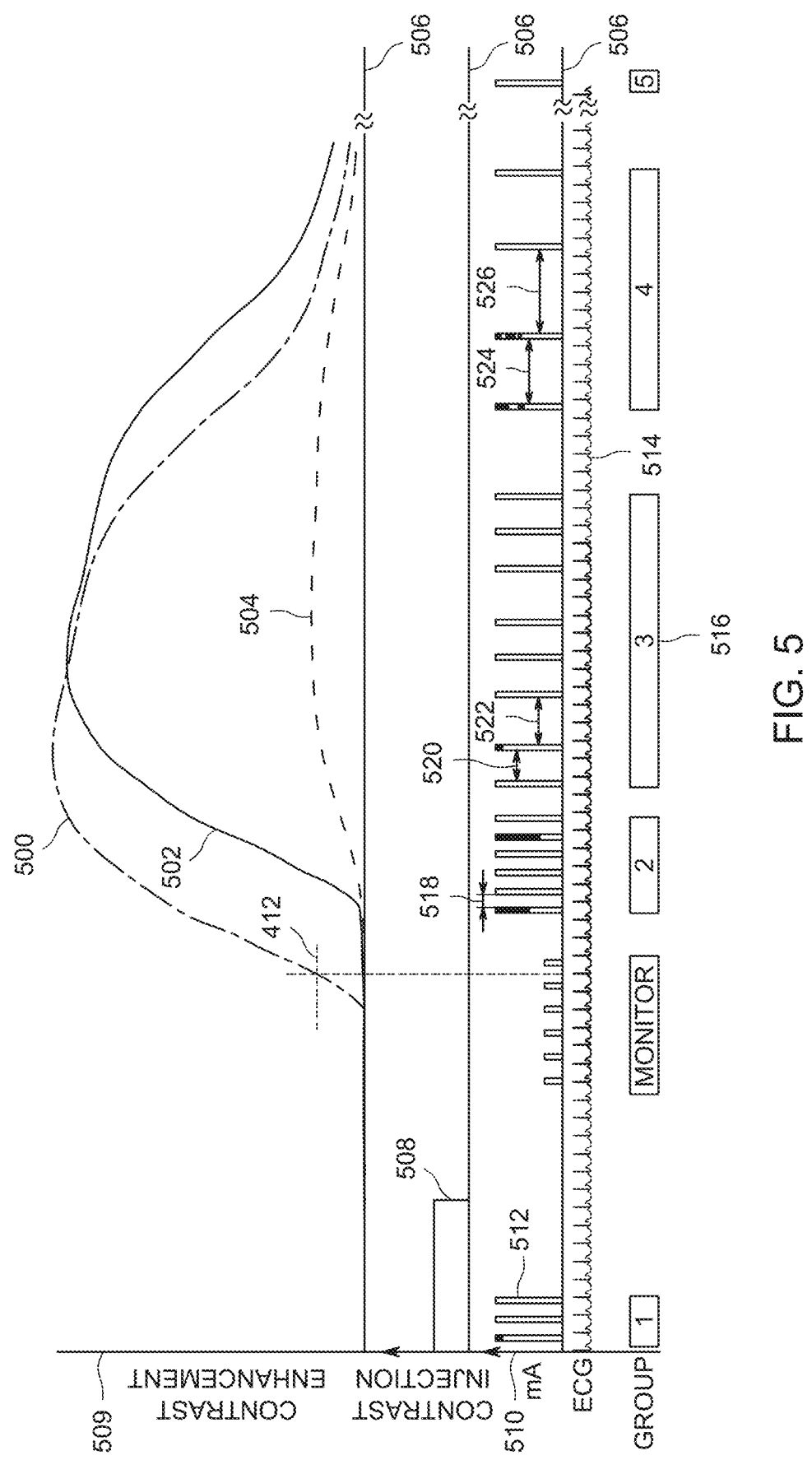
FIG. 5 illustrates another example of contrast levels measured in different monitor locations of an imaged body.

FIG. 5 illustrates another example of contrast levels 500, 502, 504 measured in different monitor locations of an imaged body. The contrast levels 500, 502, 504 are shown alongside a horizontal axis 506 representative of time and alongside a vertical axis 509 representative of increasing amounts of contrast in the imaged body. The contrast levels 500 can represent the measured amount of contrast in the pulmonary artery of a patient, the contrast levels 502 can represent the measured amount of contrast in the aorta of the patient, and the contrast levels 504 can represent the measured amount of contrast in one or more locations of the myocardium of the patient.

Also shown in FIG. 5 is a contrast injection bar 508. This injection bar 508 indicates the time period over which the contrast agent is administered to the patient. For example, the time period along the horizontal axis 506 over which the injection bar 508 extends indicates when and how long the contrast agent is injected into the patient.

Several tube pulses 512 also are shown in FIG. 5 alongside another horizontal axis 506 representative of time. These pulses 512 indicate when the tube 115 is energized by the generator 113 of imaging system to generate one or more exposures of imaging radiation toward the patient. For example, the pulses 512 in FIG. 5 can indicate when x-rays are generated and directed toward one or more regions of interest in the patient. The pulses 512 also are shown alongside a vertical axis 510 that represents the magnitude of the energy at which the tube 115 is energized. Taller pulses 512 in FIG. 5 indicate radiation doses with greater energy being generated by the tube 115, while shorter pulses 512 in FIG. 5 indicate radiation doses being generated by the tube 115 with less energy.

Also shown in FIG. 5 is an electrocardiogram signal 514. This is signal 514 can be measured by the sensor 124 shown in FIG. 1. The signal 514 can be used to measure or otherwise determine the timing of cardiac cycles of the patient. As described above, the inter-scan timing between exposures (for example, between the pulses 512) can be based on the heart rate, and therefore, the signal 514 that is monitored by the processing unit 120. FIG. 5 also illustrates several group boxes 516. These group boxes 516 indicate which imaging group is being acquired at different times. For example, because the box 516 labeled "1" occurs to the farthest left along the horizontal axis 506, this indicates that the first imaging group (for example, the scout images) is obtained first. The box 516 labeled "monitor" represents the pulses 512 used to obtain the monitor images described above. The boxes 516 labeled "2", "3", "4,", and "5" represent the pulses 512 used to obtain the scans within each corresponding image group.

Several different inter-scan timings 518, 520, 522, 524, 526 are shown in FIG. 5 between the tube pulses 512. As shown, these inter-scan timings 518 can be constant within an imaging group, such as during the monitor group or the second group in FIG. 5. With respect to the third group of images, the inter-scan timings 520, 522 can vary or otherwise change between consecutive pulses 512 of the tube 115. Similarly, with respect to the fourth imaging group, the inter-scan timings 524, 526 also may change over time.

In the example of FIG. 5, the processing unit 120 can begin a scan series having the first through fifth image groups and also begin the administration of an intravenous contrast agent, as indicated by the injection box 508. The processing unit 120 directs the generator 113 to begin a group of three cardiac-gated baseline scans to generate baseline images (described above) using the pulses 512 in the first imaging group. Obtaining multiple baseline images can help ensure accuracy in case of an irregular heartbeat or patient motion during one or more of the pulses 512 in the first group.

The processing unit 120 can direct the generator 113 to create the pulses 512 every heart beat based on the signal 514. If the heart rate is sufficiently high that the CT acquisition unit 110 cannot generate a pulse 512 every heartbeat, then the processing unit 120 can direct the CT acquisition unit 110 to generate a pulse 512 every other beat or every third beat, or the like.

Following administration of the contrast agent, the processing unit 120 can direct the generator 113 to begin a sequence of monitoring pulses 512 within the monitoring group 516. These monitoring pulses 512 are sensed by the detector 114 to create the monitor images described above. The contrast levels 500, 502, 504 in one or more monitoring locations (e.g., the pulmonary artery, the aorta, and the myocardium) are measured from these monitor images. The entrance criteria for the illustrated example can include passage of the contrast level 500 in the pulmonary artery above the designated contrast level threshold 412, as shown in FIG. 5.

Once the measured contrast level 500 and the pulmonary artery exceeds the contrast level threshold 412, the processing unit 120 may wait for a designated temporal delay before directing the generator 113 to begin generating the pulses 512 of the second imaging group 516. In this second imaging group 516, the processing unit 120 may use a constant or unchanging inter-scan delay 518 with the pulses 512 being generated relatively rapidly, such as once every heartbeat. The processing unit 120 can continue measuring the contrast levels 502 and/or 504 during the second imaging group 516 to determine when the contrast agent arrives at various portions of the myocardium.

In the illustrated embodiment, the exit or transition criteria for the second imaging group 516 are met when a designated number of pulses are generated. For example, the second imaging group may end once six imaging scans are performed, as shown in FIG. 5. Once this threshold limit of pulses 512 is reached, the processing unit 120 can transition to the third imaging group 516.

During the third imaging group 516, the processing unit 120 can dynamically change the inter-scan delays 520, 522 between the pulses 512. As one example, the processing unit 120 can vary the inter-scan delays 520, 522 as a function of a desired or designated inter-scan delay and the heart rate of the patient. For example, the inter-scan delays 520, 522 can be calculated as:

$$ISD = t_1 + (t_{desig} * (N-1)) - t_{N-1} - t_{R\,to\,R/2}$$

where ISD represents the varying or dynamically changing inter-scan delay, $t_1$ represents the starting time of the first exposure in the current imaging group, $t_{desig}$ represents a designated or selected inter-scan delay (e.g., two seconds), N represents the number of the next exposure in the current imaging group, $t_{N-1}$ represents the time at the end of the previous exposure in the imaging group, and $t_{R\,to\,R/2}$ represents half of the predicted interval between R waves in the ECG signal 514 (e.g., the time between the start of two consecutive heart beats).

Once the measured contrast level 500 and the pulmonary artery exceeds the contrast level threshold 412, the processing unit 120 may wait for a designated temporal delay before directing the generator 113 to begin generating the pulses 512 of the second imaging group 516. In this second imaging group 516, the processing unit 120 may use a constant or unchanging inter-scan delay 518 with the pulses 512 being generated relatively rapidly, such as once every heartbeat. The processing unit 120 can continue measuring the contrast levels 502 and/or 504 during the second imaging group 516 to determine when the contrast agent arrives at various portions of the myocardium.

As described above, the exit criteria for one or more imaging groups 516 can be based on the times of previous imaging groups. In the illustrated example, the third imaging group 516 may end at a time that is 1.75 times the time delay between administering the contrast agent and the time at which the second imaging group 516 began. For example, if the second imaging group 516 started at twenty seconds following administration of the contrast agent, then the third imaging group 516 may end at thirty-five seconds following administration of the contrast agent. As another example, if the second imaging group 516 starts twenty-eight seconds after administration of the contrast agent, then the third imaging group 516 will continue until forty-nine seconds after administration of the contrast agent.

The processing unit 120 can then transition to the fourth imaging group 516, where the scan pulses 512 occur with inter-scan delays 524, 526 that are selected so that the average of the inter-scan delays 524, 526 within this group is a designated inter-scan delay, such as four seconds or five cardiac cycles of the patient in the signal 514. The processing unit 120 can then transition to the fifth imaging group 516, where a single scan pulse 512 is generated.

Varying the inter-scan delay for scan pulses within an imaging group can help ensure that the imaging exposures occur at the correct phases of the cardiac cycle of a patient. This can allow for the imaging system 100 to acquire the needed images to examine the region of interest in the patient in a shorter time period, with fewer re-scans, and with less radiation exposure relative to imaging groups having all fixed inter-scan delays.

FIG. 6 is a block schematic diagram of one example of a CT imaging system 900 that may be utilized to implement various embodiments discussed herein. The imaging system 900 can represent another embodiment of the imaging system 100 shown in FIG. 1. Although the CT imaging system 900 is illustrated as a standalone imaging system, the CT imaging system 900 may form part of a multi-modality imaging system in some embodiments. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 and a bowtie filter module 915 are provided proximate the X-ray source 912. In various embodiments, the source collimator 913 may be configured to provide wide collimation as discussed herein. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917.

The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

The depicted detector array 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 6 shows only a single row of detector elements 916 (i.e., a detector row). However, the multi-slice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 160 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the example embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view" or "projection." A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360-degree view may be obtained using less than a complete revolution.

In one embodiment, a method includes acquiring one or more non-contrast images of a region of interest in an imaged body and determining an entrance criterion based on the one or more non-contrast images. The entrance criterion dictates one or more conditions in which to begin acquiring one or more groups of contrast imaging exposures of the region of interest in the imaged body. The method also includes measuring an amount of a contrast agent in one or more locations in the imaged body subsequent to acquiring the one or more non-contrast images of the region of interest in the imaged body, determining that the one or more conditions of the entrance criterion are met based on the amount of the contrast agent that is measured in the imaged body, and acquiring one or more contrast images of the region of interest in the imaged body responsive to determining that the one or more conditions of the entrance criterion are met.

Optionally, the entrance criterion designates one or more non-zero contrast level thresholds associated with different locations in the region of interest, and the one or more contrast images of the region of interest are acquired responsive to the amount of the contrast agent that is measured at the different locations being at or above the one or more non-zero contrast level thresholds associated with the different locations.

Optionally, the entrance criterion designates a rate of change in the amount of the contrast agent that is measured.

Optionally, the entrance criterion designates a peak in changes in the amount of contrast agent with respect to time.

Optionally, the entrance criterion designates one or more of a positive or negative rate of change in the amount of contrast agent with respect to time.

Optionally, the method also includes determining an exit criterion that dictates one or more conditions in which to one or more of stop acquiring at least one of the groups of the imaging exposures of the region of interest in the imaged body or transition between acquiring two or more of the groups of the imaging exposures of the region of interest in the imaged body.

Optionally, the entrance criterion includes a temporal delay following commencement or completion of a previous group of the imaging exposures of the imaged body before the one or more groups of the contrast imaging exposures are acquired.

Optionally, the one or more groups of the contrast imaging exposures include a temporal delay between the contrast imaging exposures of the region of interest in the imaged body.

Optionally, the temporal delay is one of plural different temporal delays between the contrast imaging exposures. The method also can include automatically changing the different temporal delays such that one or more of an average or a median of the different temporal delays is a designated temporal delay.

In one embodiment, an imaging system includes one or more processors configured to examine one or more non-contrast images of a region of interest in an imaged body and to determine an entrance criterion based on the one or more non-contrast images. The entrance criterion dictates one or more conditions in which to begin acquiring one or more groups of contrast imaging exposures of the region of interest in the imaged body. The one or more processors also are configured to measure an amount of a contrast agent in one or more locations in the imaged body after acquiring the one or more non-contrast images of the region of interest in the imaged body and to determine that the one or more conditions of the entrance criterion are met based on the amount of the contrast agent that is measured in the imaged body. The one or more processors also are configured to direct an imaging source and an imaging detector to acquire one or more contrast images of the region of interest in the imaged body responsive to determining that the one or more conditions of the entrance criterion are met.

Optionally, the entrance criterion designates one or more non-zero contrast level thresholds associated with different locations in the region of interest. The one or more processors also can be configured to direct the imaging source and the imaging detector to acquire the one or more contrast images of the region of interest responsive to the amount of the contrast agent that is measured at the different locations being at or above the one or more non-zero contrast level thresholds associated with the different locations.

Optionally, the entrance criterion designates a rate of change in the amount of the contrast agent that is measured.

Optionally, the one or more processors are configured to change a rate at which the one or more contrast images are acquired based on the rate of change in the amount of the contrast agent that is measured.

Optionally, the entrance criterion designates a peak in changes in the amount of contrast agent with respect to time.

Optionally, the entrance criterion designates one or more of a positive or negative rate of change in the amount of contrast agent with respect to time.

In one embodiment, a method includes acquiring image data of a region of interest in an imaged body by exposing the region of interest to multiple imaging exposures within one or more groups of imaging exposures with the imaging exposures in each of the groups separated in time by one or more temporal delays, changing the one or more temporal delays in at least one of the groups of the imaging exposures based on one or more of a heart rate of a patient having the imaged body, an average or median of the one or more temporal delays, or a measured amount of a contrast agent in the imaged body, and forming one or more images of the region of interest using the image data.

Optionally, changing the one or more temporal delays includes varying durations of the one or more temporal delays with respect to time such that one or more of the average or the median of the one or more temporal delays is a designated temporal delay.

Optionally, the method also includes measuring the amount of contrast agent in the imaged body, and terminating acquisition of the image data of the region of interest prior to acquiring a designated number of the imaging exposures based on the amount of contrast agent that is measured.

Optionally, the method also can include acquiring one or more non-contrast images of the region of interest in the imaged body, and determining an entrance criterion based on the one or more non-contrast images. The entrance criterion can dictate one or more conditions in which to begin acquiring the image data from the one or more groups of the imaging exposures. The method also can include measuring the amount of contrast agent in one or more locations in the imaged body after acquiring the one or more non-contrast images of the region of interest in the imaged body, and determining that the one or more conditions of the entrance criterion are met based on the amount of the contrast agent that is measured in the imaged body. The image data is acquired responsive to determining that the one or more conditions of the entrance criterion are met.

Optionally, the entrance criterion includes a temporal delay following commencement or completion of a previous group of the imaging exposures of the imaged body before the one or more groups of the imaging exposures are acquired.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements that do not have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method comprising:
   acquiring image data of a region of interest in an imaged body by exposing the region of interest to multiple imaging exposures within one or more groups of imaging exposures with the imaging exposures in each of the groups separated in time by one or more temporal delays;
   changing the one or more temporal delays in at least one of the groups of the imaging exposures based on an average or median of the one or more temporal delays, wherein changing the one or more temporal delays includes varying durations of the one or more temporal delays with respect to time such that one or more of the average or the median of the one or more temporal delays is a designated temporal delay; and
   forming one or more images of the region of interest using the image data.

2. The method of claim 1, further comprising:
   measuring the amount of contrast agent in the imaged body; and
   terminating acquisition of the image data of the region of interest prior to acquiring a designated number of the imaging exposures based on the amount of contrast agent that is measured.

3. The method of claim 1, further comprising:
   acquiring one or more non-contrast images of the region of interest in the imaged body;
   determining an entrance criterion based on the one or more non-contrast images, the entrance criterion dictating one or more conditions in which to begin acquiring the image data from the one or more groups of the imaging exposures;
   measuring the amount of contrast agent in one or more locations in the imaged body after acquiring the one or more non-contrast images of the region of interest in the imaged body; and
   determining that the one or more conditions of the entrance criterion are met based on the amount of the contrast agent that is measured in the imaged body,
   wherein the image data is acquired responsive to determining that the one or more conditions of the entrance criterion are met.

4. The method of claim 3, wherein the entrance criterion includes a temporal delay following commencement or completion of a previous group of the imaging exposures of the imaged body before the one or more groups of the imaging exposures are acquired.

* * * * *